(12) United States Patent
Hiemenz et al.

(10) Patent No.: US 11,103,623 B2
(45) Date of Patent: Aug. 31, 2021

(54) SYSTEM FOR IMPROVING FLUID DRAINAGE

(71) Applicants: Gregory John Hiemenz, Silver Spring, MD (US); James Philip Murphy, Newtown Square, PA (US)

(72) Inventors: Gregory John Hiemenz, Silver Spring, MD (US); James Philip Murphy, Newtown Square, PA (US)

(73) Assignee: InnoVital, LLC, Calverton, MD (US)

( * ) Notice: Subject to any disclaimer, the term of this patent is extended or adjusted under 35 U.S.C. 154(b) by 211 days.

(21) Appl. No.: 16/052,099

(22) Filed: Aug. 1, 2018

(65) Prior Publication Data

US 2018/0344908 A1 Dec. 6, 2018

Related U.S. Application Data

(63) Continuation-in-part of application No. 15/608,305, filed on May 30, 2017, now Pat. No. 10,596,312.

(51) Int. Cl.

| | |
|---|---|
| *A61M 1/00* | (2006.01) |
| *A61M 1/04* | (2006.01) |
| *A61M 25/00* | (2006.01) |
| *A61M 39/20* | (2006.01) |
| *A61J 1/10* | (2006.01) |
| *A61M 39/12* | (2006.01) |

(Continued)

(52) U.S. Cl.
CPC .............. *A61M 1/0062* (2013.01); *A61J 1/10* (2013.01); *A61M 1/0035* (2014.02); *A61M 1/0064* (2013.01); *A61M 1/04* (2013.01); *A61M 3/0208* (2014.02); *A61M 3/0241* (2013.01); *A61M 25/0017* (2013.01); *A61M 39/12* (2013.01); *A61M 39/20* (2013.01); *A61M 1/0013* (2013.01); *A61M 3/0216* (2014.02); *A61M 2039/1077* (2013.01); *A61M 2202/0413* (2013.01); *A61M 2210/101* (2013.01)

(58) Field of Classification Search
CPC .............. A61M 1/0013; A61M 1/0035; A61M 1/0062; A61M 1/0064; A61M 1/04; A61M 39/12; A61M 39/20
See application file for complete search history.

(56) References Cited

U.S. PATENT DOCUMENTS

| 4,661,110 A * | 4/1987 | Fortier | A61M 39/20 |
|---|---|---|---|
| | | | 604/256 |
| 2003/0153897 A1* | 8/2003 | Russo | A61M 39/045 |
| | | | 604/537 |

(Continued)

*Primary Examiner* — Rebecca E Eisenberg
(74) *Attorney, Agent, or Firm* — Royal W. Craig; Gordon Feinblatt LLC

(57) ABSTRACT

A low-cost and simple-to-use system and method to facilitate a prophylactic pleural lavage protocol at the time of thoracostomy tube placement for traumatic hemothorax in order to reduce the need for secondary intervention for the management of retained hemothorax. The invention may be used in conjunction with existing chest tubes and be administered at the time of initial chest tube placement, and continued at the bedside (by a bedside nurse) over the duration of chest drainage, as necessary. The system includes an operator device that semi-automatically administers a pleural lavage protocol consisting of saline instillation, and suction to slow the clotting process, prevent "gelling" of blood, and maintain drainability.

24 Claims, 7 Drawing Sheets

(51) Int. Cl.
  *A61M 3/02*  (2006.01)
  *A61M 39/10*  (2006.01)

(56) References Cited

U.S. PATENT DOCUMENTS

| | | | |
|---|---|---|---|
| 2006/0025729 A1* | 2/2006 | Leiboff | A61M 3/0208 604/317 |
| 2007/0005002 A1* | 1/2007 | Millman | A61M 1/0058 604/30 |
| 2013/0079702 A1* | 3/2013 | Klein | A61B 18/1485 604/22 |

* cited by examiner

SYSTEM FOR IMPROVING FLUID DRAINAGE

CROSS-REFERENCE TO RELATED APPLICATIONS

The present application derives priority from U.S. Provisional Patent Application 62/345,230 filed 3 Jun. 2016, and from U.S. patent application Ser. No. 15/608,305, filed 30 May 2017.

BACKGROUND OF THE INVENTION

1. Field of the Invention

The present invention relates to drainage devices for surgical procedures and, more particularly, to a system for improving drainage from a cavity within a human or animal body that breaks up clots or reduces clotting and/or thickening of the fluid to facilitate drainage.

2. Description of the Background

Trauma is the leading cause of death for US civilians under age forty with an incidence of 140,000 deaths per year. Thoracic injuries occur in approximately 60% of polytrauma cases and are a primary or contributing factor in up to 75% of all civilian trauma-related deaths. Ivey, K. M., White, C. E., Wallum, T. E., et al., 2012, "Thoracic Injuries in US Combat Casualties: A 10-Year Review Of Operation Enduring Freedom And Iraqi Freedom," J Trauma Acute Care Surg, 73(6 Sup 5): S514-S519; Mowery, et al., "Hemothorax and Occult Pneumothorax, Management of," J. Trauma, February 2011, Vol. 70, No. 2, pp. 510-518. Hemothorax, an accumulation of blood in the pleural space, is a common result of chest trauma. In the U.S. alone, the incidence of trauma-related hemothorax approaches 300,000 cases per year. Mowery et al, supra; see also, Wim G. Boersma, Jos A. Stigt, Hans J. M. Smit., Treatment of Haemothorax, Respir Med. 2010 November, 104(11): 1583-1587.

The primary treatment of hemothorax is tube thoracostomy. Thoracostomy typically involves placement of a large bore (36Fr to 42Fr) catheter (thoracostomy tube or chest tube) for drainage of the pleural space. Mowery et al, supra. Due to the likelihood of a combined pneumothorax, chest tubes for thoracic trauma are typically placed superiorly, as notionally illustrated in FIG. 1. While the majority of traumatic hemothoraces are managed by tube thoracostomy alone, in 3-30% of cases a measurable amount of blood remains in the chest after chest tube placement, a condition known as retained hemothorax, as notionally illustrated in FIG. 2. Kimbrell B J, Yamzon J, Petrone P, Asensio J A, Velmahos G C, Intrapleural Thrombolysis For The Management of Undrained Traumatic Hemothorax: A Prospective Observational Study., J Trauma 62(5):1175-9 (2007); Rezende Neto J B, Patore Neto M, Hirano E S, Rizoli S, Nascimento Jr B, Fraga G P, Management Of Retained Hemothoraces After Chest Tube Thoracostomy For Trauma. Rev Col Bras Cir. 39(4) (2012); Chou, Lin, and Wu, "Video Assisted Thoracoscopic Surgery for Retained Hemothorax in Blunt Chest Trauma," Current Opinion in Pulmonary Medicine, Vol. 21, 2015, pp. 393-398.

There are several reasons why a hemothorax may not completely drain—ranging from the sheer volume of blood, the clotting process proceeding more rapidly than the draining process, and patient positioning relative to tube position (i.e., the tube is not in the dependent position). Retained hemothorax (RH) is typically diagnosed via computed tomography (CT) with chest CT imaging often triggered by a finding of persistent x-ray opacity after tube thoracostomy. Empyema, a bacterial or frankly purulent collection in the pleural space, results in 33% percent of RH cases that are visible on x-ray even after chest tube placement (typical RH volume >500 mL). Patients with RH are 12-16 times more likely to develop post-traumatic empyema than those chest trauma patients who do not develop RH. Brims et al., "Empyema Thracis: New Insights Into An Old Disease" European Respiratory Review, Vol. 19, No. 117, pp. 220-228. As such, RH is an independent risk factor for empyema, a condition with a 15-20% mortality rate (higher in immunocomprised patients). RH is also associated with subsequent adverse outcomes such as fibrothorax and trapped lung. While the maximum size of an RH that may be managed without secondary intervention has been debated, correlations between RH size and complications such as empyema and trapped lung have driven current recommendations to administer a secondary therapy (typically surgery) for RH's larger than 500 mL or ⅓ of the hemithorax. Mowery, et al., supra, Boersma et al, supra.

While studies investigating administration of an intrapleural thrombolytic for RH have shown limited success, current recommendations call for early video assisted thorascopic surgery (VATS). 39(4). Chou et al, supra. In VATS, a thoracoscope and surgical instruments are inserted into the chest cavity via 1-3 relatively small incisions. The ipsilateral lung is collapsed to obtain a clearer view of the pleural cavity. Adhesions are then released via blunt digital dissection or sharp endoscopic electrocoagulated dissection and blood and clots are removed by standard suction or a suction-irrigator system. Sponge sticks and ring forceps can enable careful removal of organized collections and some studies have investigated the use of jet-lavage to more efficiently remove adherent clots and membranes without damaging the pleura. Early VATS has been shown to decrease the incidence of empyema and pneumonia and rapidly restore lung function. Chou et al, supra. Compared to previous surgical approaches to RH (i.e. thoracotomy), VATS has been reported to have fewer postoperative complications, less pain, fewer wound and pulmonary complications, shorter recovery time, and shorter length of hospital stay. As a result, VATS has become a preferred primary management option for RH—even over the placement of a second chest tube.

VATS intervention, however, is not without costs and contraindications. Most notably VATS requires a high level of expertise and resources—a skilled thoracic surgeon, an anesthesiologist to perform special intubation and lung drop, as well as significant support staff and equipment. Moreover, the careful removal of coagula adhering to underlying structures with limited visibility usually proves very time consuming and tiresome, and thus, costly work. Tomaselli F, Maier A, Renner H, Smolle-Juttner F M, Thoracoscopical Water Jet Lavage In Coagulated Hemothorax, Eur J Cardiothorac Surg. 23(3):424-5 (2003). In fact, these requirements for specialized equipment and personnel, as well as their associated costs, have been noted as barriers to widespread use of VATS. Milanchi, S., Makey, I., McKenna, R., & Margulies, D. R., "Video-Assisted Thoracoscopic Surgery in the Management of Penetrating And Blunt Thoracic Trauma, Journal of Minimal Access Surgery, 5(3), 63-66. Because it requires single-lung anesthesia, VATS is not only costly and time consuming, but also contraindicated for hemodynamic instability. VATS is also contraindicated for patients with spinal injuries and pulmonary disease or otherwise compromised lung function. Milanchi et al, supra.

It would be preferable to avoid the need for surgical intervention by actively preventing an RH and improving the drainage performance of conventional tube thoracostomy. While attempts at actively clearing the chest tube via Fogarty balloon catheters and other active clearance products have shown some reduction in the amount of retained blood, these devices do little to improve drainage of fluid beyond the distal tip of the chest tube. Boyacioglu, et al., "A New Use of Fogarty Catheter: Chest Tube Clearance," Heart, Lung and Circulation, Vol. 23, pp. e229-230 (2004); Shiose, et al., "Improved Drainage with Active Chest Tube Clearance," Interactive Cardiovascular Thoracic Surgery, Vol. 10, No. 5, pp 685-688 (2010).

Additionally, the use of a sterile suction catheter to evacuate the pleural space prior to chest tube insertion has shown modest reduction in duration of tube drainage and need for secondary intervention. Interestingly, a limited recent study demonstrated a lower rate of secondary intervention after prophylactic pleural lavage using warm saline at the time of thoracostomy tube placement and suctioning via a suction catheter advanced into the thoracostomy tube. Kugler, N. W., Carver, T. W., and Paul, J. S., "Prophylactive Pleural Lavage Decreases Secondary Intervention in Patients with Traumatic Hemothorax," ASCA 39.09; Kugler N W, Carver T W, Milia D J, Paul J S, "Thoracic Irrigation Prevents Retained Hemothorax: A Prospective Propensity Score Matched Analysis," Presented at Western Trauma Association. Mar. 6, 2016.

Despite an array of successful clinical results most trauma surgeons do not regularly perform thoracic lavage due to real or perceived difficulty and time intensity of the manual procedure, insterility of the procedure, or other reasons. What is needed is a flexible, low-cost and easy-to-use system that enables rapid pleural lavage via the existing chest tube in a completely sterile manner.

SUMMARY OF THE INVENTION

It is, therefore, a primary object of the present invention to provide a system and method for pleural lavage, both at the time of thoracostomy tube placement and subsequent to tube placement, for traumatic hemothorax in order to reduce the need for secondary intervention for the management of retained hemothorax.

It is another object to provide a system and method as above that is simple and efficient to use, employing familiar tubing connections and control valves, and which deploys a rapid, automated saline infusion process, thereby minimizing training requirements and barriers to adoption.

It is another object to provide a system and method to facilitate a prophylactic pleural lavage as above that enables easy transition from lavage, to high wall suction, to low pressure chest drain suction without breaking the sterile circuit.

It is still another object to provide a system and method that allows adjustment of the lavage protocol (e.g., amount of infused saline per lavage cycle, number of lavage cycles at time of tube placement), and repetition of lavage at a later time based upon clinical indications.

It is still another object to provide a system and method that allows other future therapies/procedures to be administered through the chest tube without breaking the sterile circuit, such as introduction of a fibrinolytic solution, the use of a balloon catheter for tube clearance and/or pneumatic agitation at the distal tip of the chest tube, etc.

In accordance with the foregoing objects, the invention disclosed herein is a low-cost and simple-to-use system and method to facilitate a prophylactic pleural lavage protocol at the time of thoracostomy tube placement for traumatic hemothorax in order to reduce the need for secondary intervention for the management of retained hemothorax. The invention may be used in conjunction with existing chest tubes and be administered at the time of initial chest tube placement, and continued at the bedside (by a bedside nurse) over the duration of chest drainage, as necessary. The system includes a lavage controller that semi-automatically administers a pleural lavage protocol consisting of instillation of warmed saline into the pleural space and suction to slow the clotting process, prevent "gelling" of blood, and maintain drainability.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

The present invention is a system to facilitate a rapid pleural lavage protocol via a thoracostomy tube in order to the system improve drainage of a patient's pleural space. One skilled in the art should understand that the system could be used for other applications and for other indications, such as pleural effusions (hydrothorax, chylothorax, pyothorax/empyema, urinothorax, etc).

Figure 1:
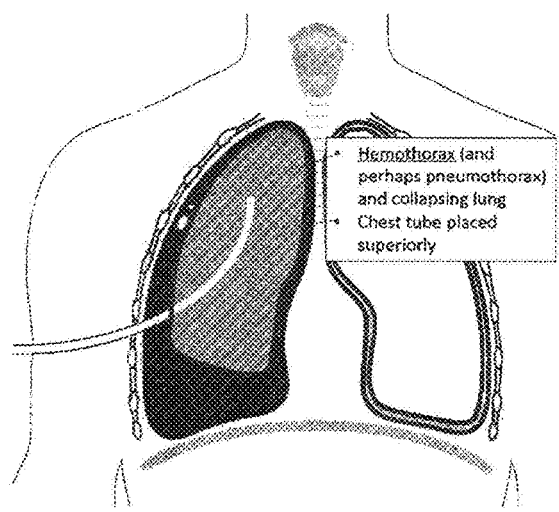
FIG. 1 is a perspective diagram illustrating a chest tube initially placed superiorly.
Figure 2:
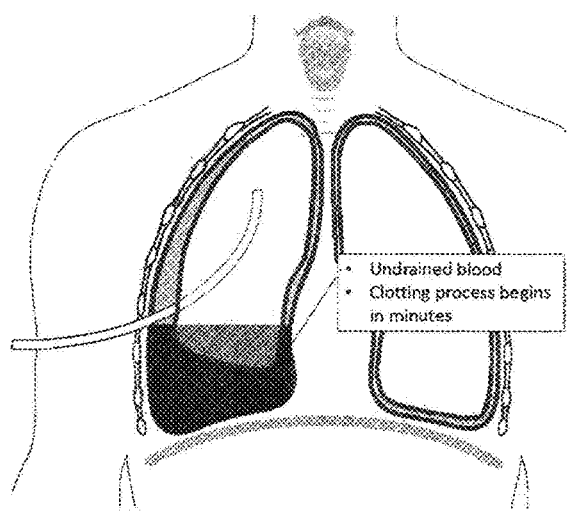
FIG. 2 is a perspective diagram illustrating how undrained blood tends to remain in the lower and posterior pleural space.
Figure 3:
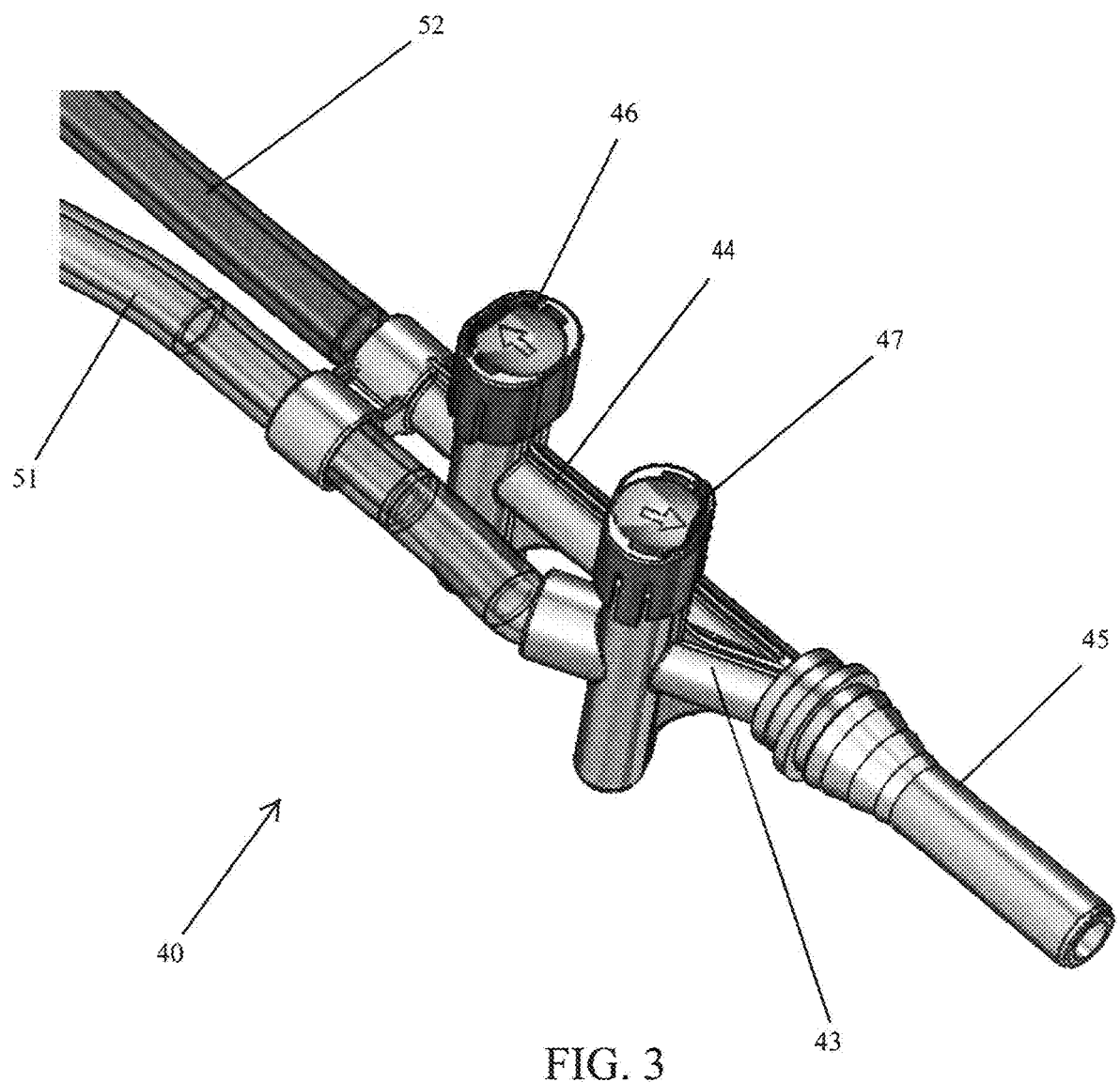
FIG. 3 is a perspective drawing of the lavage controller according to an embodiment of the present invention.

FIG. 3 depicts a two-channel pleural lavage controller 40 which, in operation, would be connected in fluid communication with a fluid source (not shown) such as a saline bag, and a suction source (not shown), such as hospital wall suction, via tubes 51 and 52, respectively. Channels 43 and 44 are manifolded to a single nozzle 45 which connects to a standard chest tube through a novel Y-port, as will be described, for administering a protocol consisting of saline instillation, chest drainage, and suction to facilitate drainage of the pleural space.

A fluid source according to a preferred embodiment of the present invention is a saline bag that is pressurized by passive means such as gravity or ambient air pressure. For example, the saline infuser may consist of simply a saline bag that is hung at a height above the patient such that it passively flows into the patient's pleural space. Similarly, the fluid source may simply be a funnel into which saline is poured. Preferably the fluid source and system should be configured for emptying a 1000 cc saline bag in at most 30 seconds, and optimally should be configured for emptying the same 1000 cc bag in 20 seconds, the latter enabling a 500 cc lavage in 10 seconds. It is also preferable for the saline to be warmed to substantially average body temperature prior to infusion. In another embodiment, the saline infuser comprises a commercially available rapid infuser by Level 1™, Inc., which includes a fast flow rate fluid warmer capable of sustained flow rates in a range of from 30 ml/min to 1100 ml/min with a maximal rate of 1400 ml/min through a small bore peripheral venous catheter (typically 20 gauge needle with 0.6 mm internal diameter). These flow rate specifications depend on Poiseuille's law, the variables being the internal diameter (D) and length (L) of the chest tube, the viscosity of the liquid (h) and the pressure of the saline infuser. If the diameter of a tube is doubled, flow will increase by a factor of 16, implying that small increases in the size of drainage tubes will result in large increases in flow rates. Traditionally, large bore (>28F, 9 mm internal diameter) catheters are recommended in almost all situations that required chest drainage. Given the substantial difference in internal diameter between a peripheral venous catheter and traditional thoracostomy tube, the rapid infuser will be capable of providing significantly higher flow rates through a thoracostomy tube. Similar commercial products are available from Belmont™ or Thermacor™. Alternatively, a manual pressure infusion bag may be used such as the Infu-Surg® pressure infusion bag. Manual pressure infusion bags are very low cost and ubiquitous at hospitals, and operate in the same manner and at the same pressures (~300 mmHg) as the above-described rapid infusers. However, they lack the automation for warming and pressurizing the saline. Nevertheless, tests conducted by the present inventors demonstrated that, when pressurized to 300 mmHg, a manual pressure infusion bag was likewise capable of emptying a 1000 cc the same bag in 20 seconds. Still another option for the saline infuser is to use a suction/irrigation pump such as the StrykeFlow™ II system manufactured by Stryker, or a Stryker AHTO system. The StrykeFlow II is a battery-operated, fully disposable fixed-flow-rate pump that hangs from the saline bag and operates by generating negative pressure within the tubing to draw fluid from the IV bag. The Stryker AHTO, on the other hand, features a reusable pump, with three flow rate settings up to 4 L/min. However, the goal here is to impart a 500 mL lavage in just a few seconds and current surgical irrigation pumps are less-well suited for this Also in a preferred embodiment, a suction source may be a hospital central suction system connected via wall units that are typical in hospital rooms and typically comprise a connection port, a pressure regulator, and a collection bottle. This type of suction source is typically referred to as "wall suction". In another embodiment, the suction source may be a conventional surgical suction pump may be used such as a Medala™ Basic. These suction sources may be connected directly to the lavage controller suction tube 52 or by way of a chest drainage system, such as an Atrium Oasis™ Dry Suction Drain or TeleFlex Pluer-evac® Chest Drainage System, which typically comprise a collection reservoir, a pressure regulator, and seal to prevent air or fluid from entering the pleural space. In this latter case, the additional chest drainage system would be placed between the suction source and the lavage controller suction tube 52.

As shown in FIG. 3, nozzle 45 of lavage controller 40 comprises a frustoconically-shaped outward protrusion that tapers towards a distal end opposite channels 43, 44 along its entire length or for a portion of its length, thereafter taking the shape of a cylinder. Nozzle 45 may comprise annular-exterior ribs or steps along all or part of its length to facilitate cooperative engagement with Y-port 60, or with a standard chest tube, as will be described. Along its entire length, nozzle 45 is defined by a central lumen. The frustoconical shape enables connection to Y-port 60 or to variously-sized tubes and the annular ribs/steps prevent dislodgement of the tubes or valve(s) once inserted thereon.

On the opposite side of controller 40, ports 43, 44 may also terminate in frustoconically-shaped outward protrusions such as that described herein with respect to nozzle 45 or, alternatively, may utilize any male or female tubing coupling known in the art.

Also as seen in FIG. 3, the two channels 43, 44 are aligned with and in fluid communication with nozzle 45, axially converging at shallow angles not exceeding 45 degrees to ensure "soft" fluid branching there through, effectively reducing the risk of clogging by minimizing torturous fluid pathways. Each channel 43, 44 is equipped with a spring-return locking detent valve 46, 47 for stopping or allowing fluid flow from each nozzle 42-43 to nozzle 45. The spring-return locking detent valves 46, 47 may be marked with proper indicia for designating the channel 43, 44 and/or the desired direction of fluid or air flow there through, both to indicate which channel 43, 44 is being actuated and which tube to connect. Similarly, the nozzle 45 may be marked with proper indicia to indicate connection of Y-port or chest tube.

Figure 5:
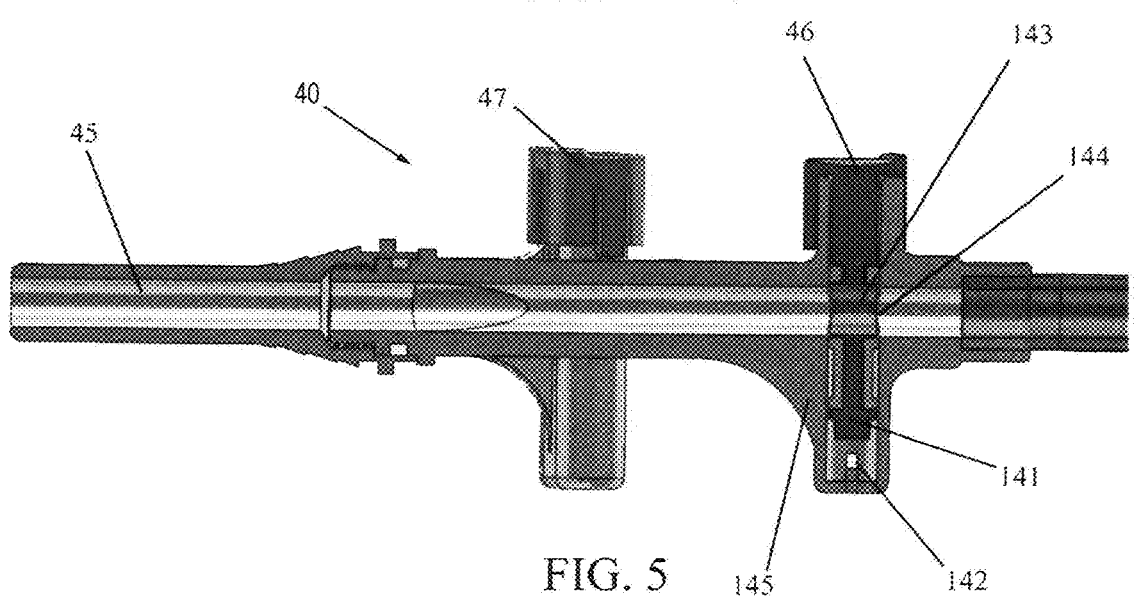
FIG. 5 is a side cutaway view of the lavage controller shown in FIG. 3.
Figure 6:
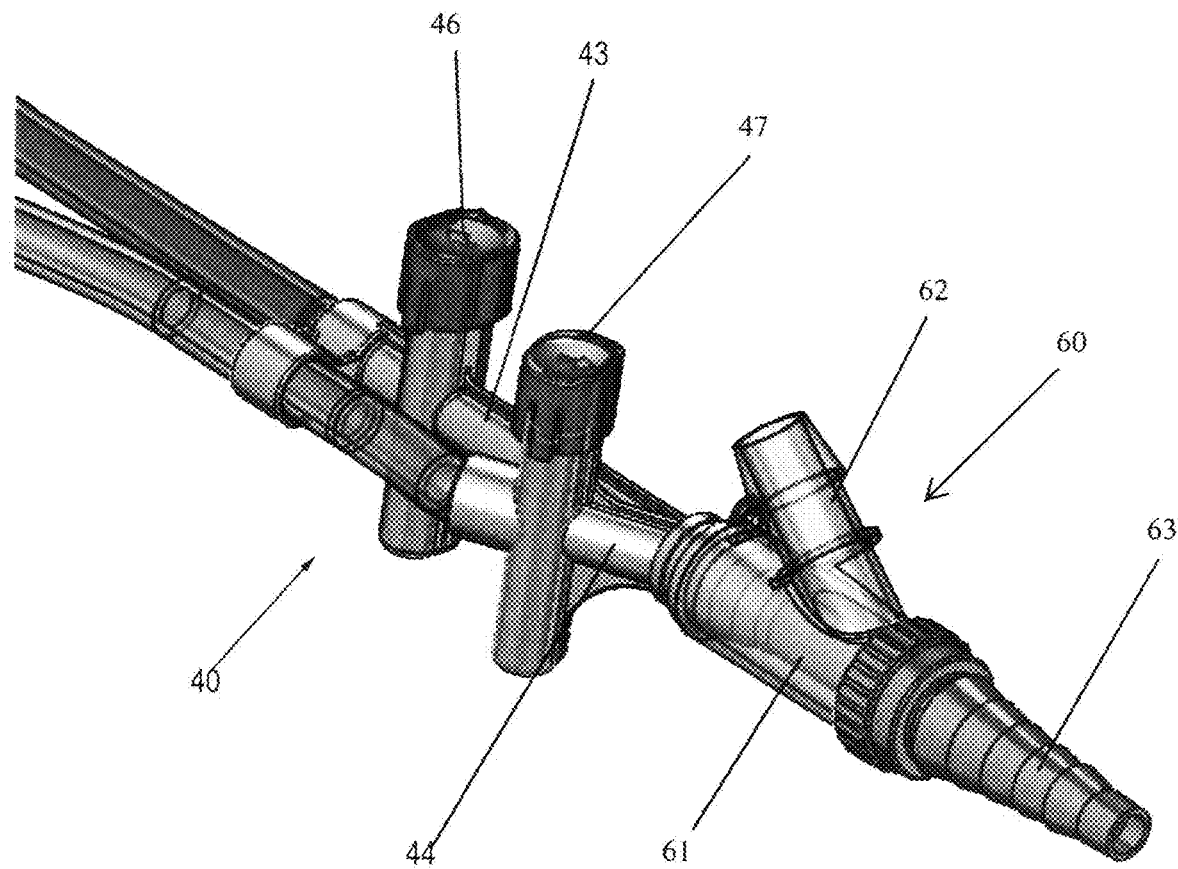
FIG. 6 is a perspective illustration of lavage controller 40 shown docked within Y-port 60 according to the present invention.

FIG. 5 is a side cutaway view of lavage controller 40 showing the operation of an exemplary spring-return locking detent valve, 46, 47. In this preferred embodiment, detent valves 46, 47 comprise an oval open-bottom button with a closed top and vertical sidewalls. The sidewalls slide vertically into a tubular receptacle formed in valve housing 145. A vertical post 141 protrudes downward from the top of the button into a tubular receptacle formed in housing 145, which serves to selectively allow/stop fluid flow. A spring 142 underlies the post 141 and biases it to a normally-closed upward position shown. However, the post 141 has an aperture 143 traversing it, which aperture 143 aligns with a conduit 144 through the housing 145 when the button and post 141 are depressed to allow fluid flow.

The illustrated detent valves 46-47 are preferably all biased by spring 142 to their normally-closed position. This generally prevents suction or lavage channels from inadvertent locking in an open position. However, it may be desirable to lock one or more valves 46-47 in an open position. Any suitable locking arrangement may be used for this. For example, the valve 46-47 button may include an extensional flap or strap to engage a cooperating feature on the valve body 145. Alternatively a more complicated push-to-lock mechanism may be used similar to those in retractable pens. A variety of such mechanical locking means are disclosed such as by U.S. Pat. No. 8,157,242. Conversely, it may be desirable to lock all ports in a closed position to prevent someone from inadvertently introducing therapy. Again, any suitable locking arrangement may be used for this. For example, while in their normally-closed (up) position the spring-return locking detent valves 46, 47 may be twisted so that it no longer fits back inside the tubular receptacle formed in housing 145. Optionally, it may be desirable to prevent someone from opening more than one detent valve 46, 47 at any time. A mutually exclusive locking arrangement can be accomplished with a suitable protrusion from each valve button that will interfere with a cooperating protrusion on another button if depressed.

Figure 4:
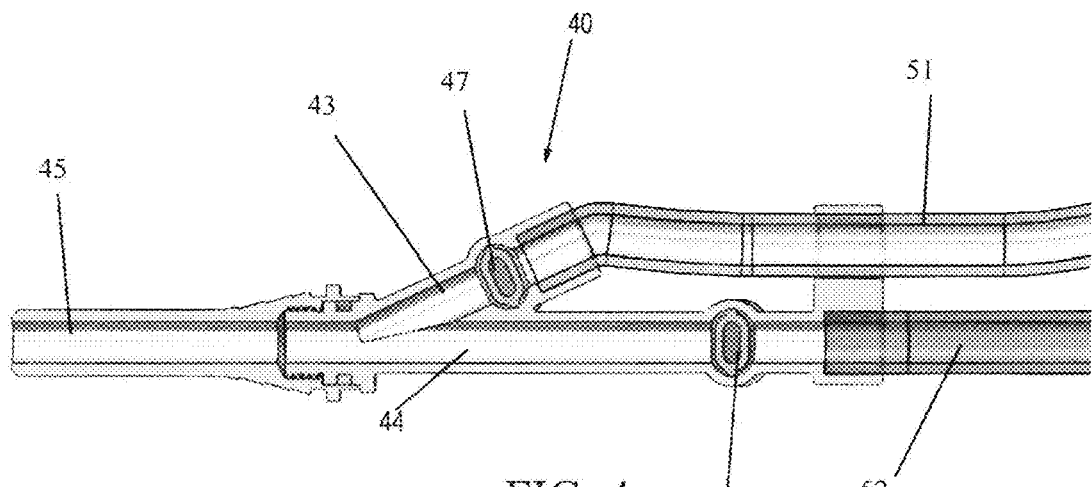
FIG. 4 is a top cutaway view of the lavage controller shown in FIG. 3.

In addition to the fluid source and suction sources connected to the lavage controller tubes 51, 52, a suction source, such as those described above, may also be connected via Y-port connection as illustrated in FIG. 4.

Figure 8:
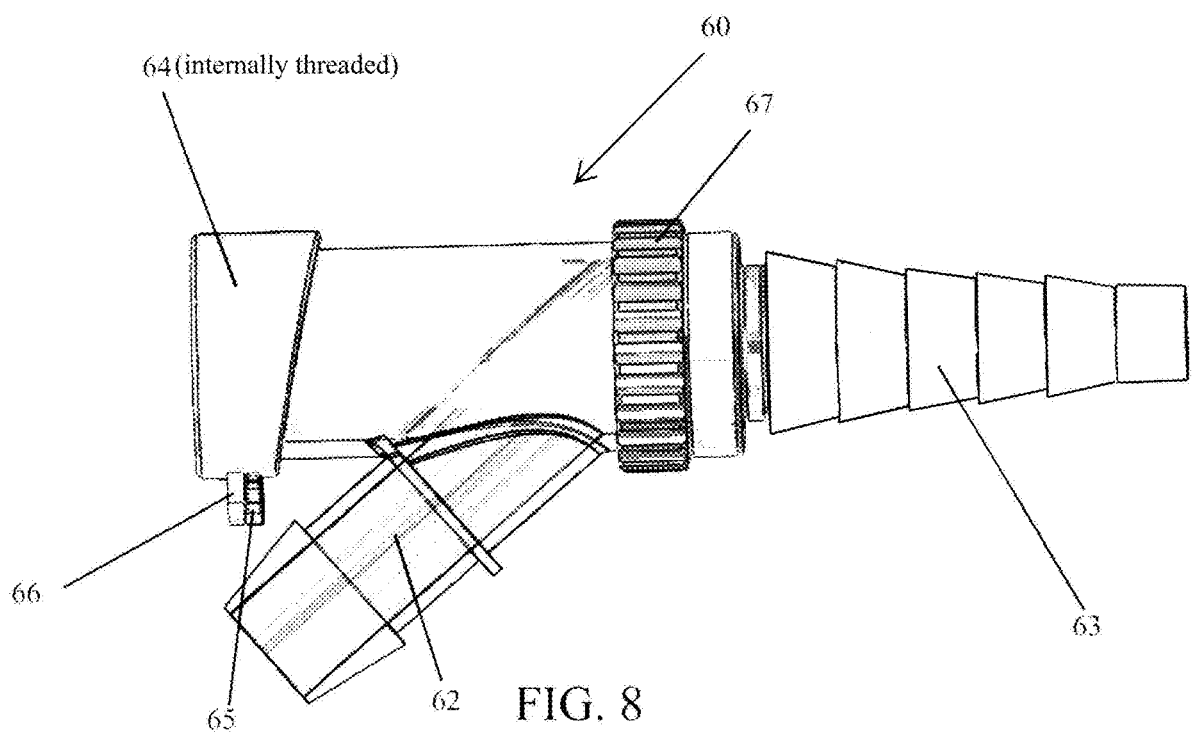
FIG. 8 is a side perspective view of Y-port 60 shown with removable cap and plug 64.
Figure 9:
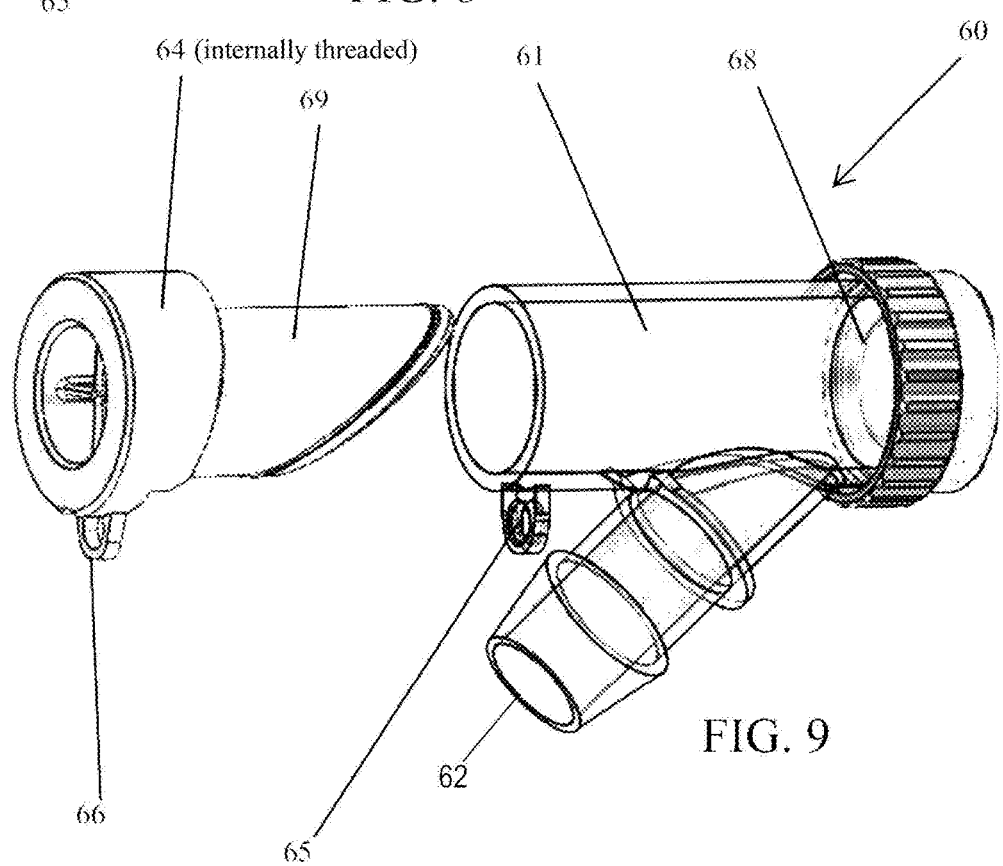
FIG. 9 is a side exploded view of Y-port 60 and cap 64 showing how plug 69 seats inside of and fills the dead space of Y-port body 61.

FIGS. 8-9 illustrate Y-port 60, which is preferably left with a single patient, in fluid communication with, and forming a sterile connection with, his or her chest tube so that later access through the chest tube is feasible without disconnecting the circuit. Y-port 60 comprises, at one end, a fitting 63 for connection to a standard chest tube. Fitting 63 may take a form similar to nozzle 45 (FIGS. 4-5) for lavage controller 40 as described above. Y-port 60 extends away from the distal end of fitting 63 into a first channel 61 comprised of a hollow, cylinder for acceptance of nozzle 45 of lavage controller 40 (FIGS. 4-5). A second channel 62 branches off from and is in fluid communication with the first channel 61 at an acute angle from first channel 61 (obtuse to fitting 63) to minimize fluid turbulence of fluids flowing through Y-port 60 similarly to the operation of controller 40, as described above. In preferred embodiments, second channel 62 is shaped and sized for a water- and air-tight connection with additional tubing to a suction source, either directly or by way of a chest drainage system as described above for lavage controller 40, and fitting 63 is sized and shaped to cooperatively fit with a standard chest tube.

Under normal use, Y-port connects the patient's chest tube to a suction source to enable continuous draining of fluid from the pleural space. Under this operation, it may be desirable to insert cap 64 into the first channel 61 of Y-port 60 to prevent the leaking of fluids from the device. Cap 64 preferably comprises a circular base with a solid, cylindrical plug 69 cooperatively sized to the interior of first channel 61 and which may be truncated at an angle as shown in FIGS. 8-9 away from the opening of second channel 62 to maintain a consistent diameter fluid flow pathway between the chest tube and the suction source connected to the distal end of second channel 62. Cap 64 and first channel 61 may have cooperatively positioned cap lock protrusions 65, 66 which align when the cap 64 is positioned correctly inside the first channel 61 of Y-port 60 to provide such a consistent diameter fluid flow pathway. Thus, cap lock 65, 66 assist the nurse or doctor in properly positioning cap 64 and may also include holes there through for the placement of a pin or other locking feature to prevent cap 64 from inadvertently being removed or to control access to provision through chest tube 50. First fluid channel 61 and fitting 63 of Y-port 60 may be independently formed, such as via injection-molding or the like, and may connect with a snap fit connection 67 to allow angular rotation between first fluid channel 61 and fitting 63. The interior of snap fit connection 67 between first fluid channel 61 and fitting 62 may also have a seal 68 for fluid-tight seating of nozzle 45 of controller 40 (FIGS. 4-5) as will be described.

Figure 7:
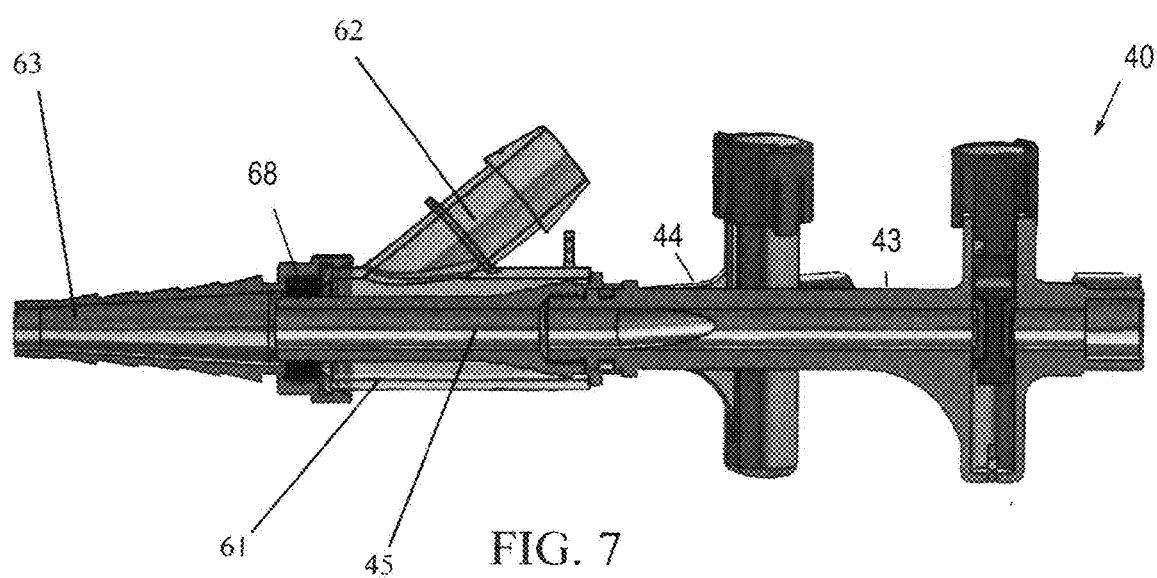
FIG. 7 is a side cutaway view of lavage controller 40 shown docked within Y-port 60 according to the present invention

Cap 64 may then be removed for connection of Y-port to lavage controller 40. Use of Y-port together with controller 40 allows for pleural lavage using warm saline at the time of thoracostomy tube placement or thereafter as needed. With specific reference to FIG. 7, nozzle 45 of controller 40 and first channel 61 and seal 68 of Y-port 60 are sized to cooperatively fit together as a male-female connection to form an fluid-tight connection between fitting 63 at the distal end of Y-port 60 (connected to chest tube) and channels 43, 44 of lavage controller 40, and by extension tubing 51, 52 and the fluid source and suction sources connected thereto, respectively. As illustrated in FIG. 7, the fluid-tight connection between the distal tip of nozzle 45 and the proximal portion of fitting 63 (via seal 68 on the inner surface of the distal end of Y-port first channel 61) creates fluid communication between the chest tube and the instrumentation connected to controller channels 43, 44 while cutting off the fluid (or air) connection between the chest tube and second channel 62 of Y-port as well as any suction source or chest drainage system connected thereto. In this way, the lavage fluid supplied from the fluid source, through lavage controller 40 via nozzle 45 and fitting 63 to the chest tube, all goes to the patient instead of being lost down the suction source or chest drainage system operatively connected to second channel 62 of Y-port 60. As stated above, at the end of the lavage/irrigation/suction procedure, controller 40 may be removed and Y-port may remain so that later access through the chest tube is feasible without disconnecting the circuit.

Figure 10:
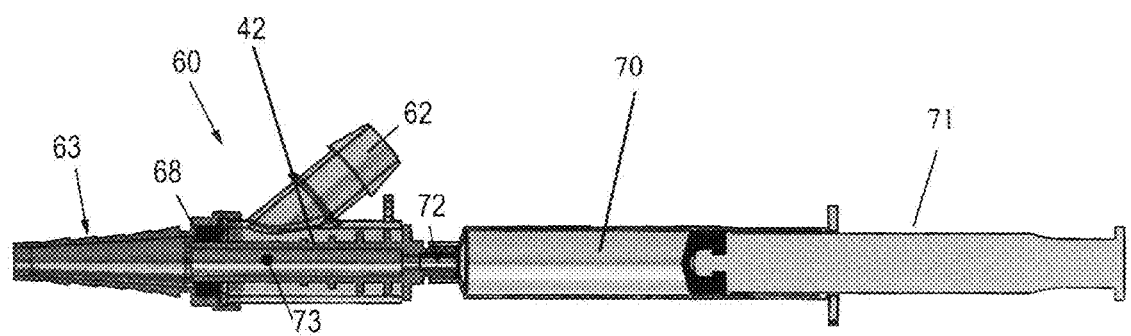
FIG. 10 is a side cutaway view of Y-port 60 engaged with another embodiment of the lavage controller 42 using a syringe 70 as a fluid source according to an embodiment of the present invention.
Figure 11:
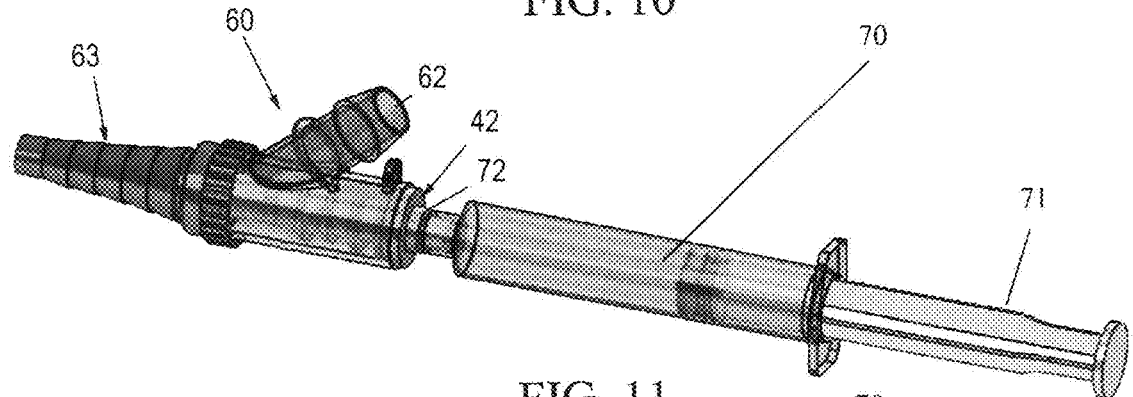
FIG. 11 is a side perspective view of Y-port 60 engaged with the lavage controller 42 of FIG. 10 using a syringe 70 as a fluid source according to an embodiment of the present invention.
Figure 12:
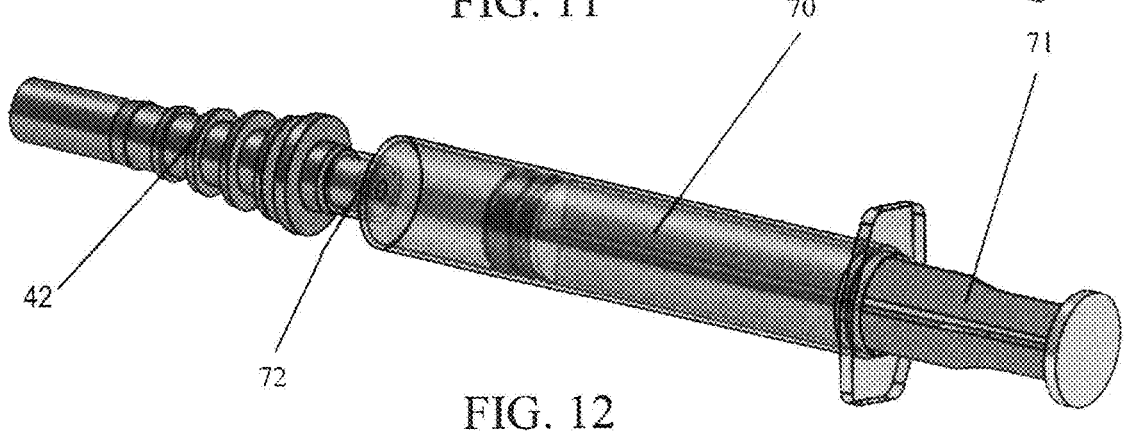
FIG. 12 is a perspective view of another embodiment of the lavage controller 42 of FIGS. 10-11 using an exemplary syringe 70 as a fluid source and for cooperative use with Y-port 60.
Figure 13:
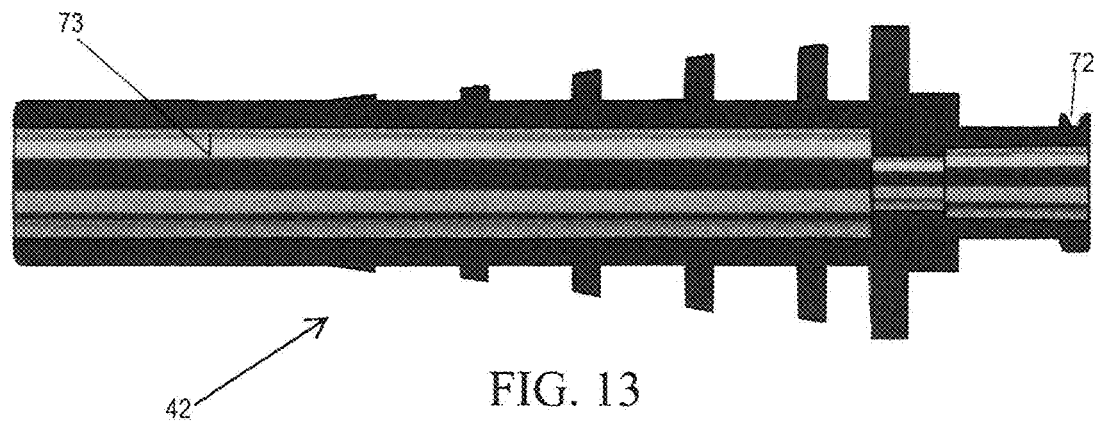
FIG. 13 is a side view of the lavage controller 42 of FIGS. 10-12 equipped with a Luer fitting 72 for connection to a syringe or other fluid source.
Figure 14:
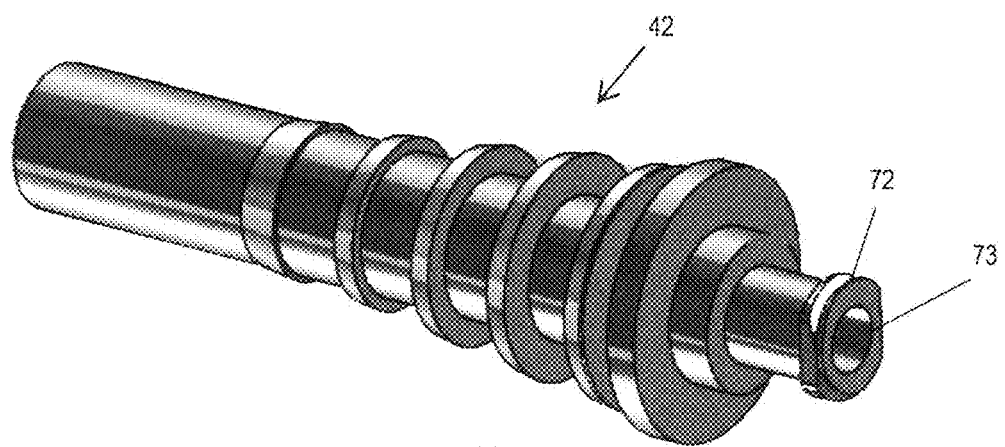
FIG. 14 is a side perspective view of the lavage controller 42 of FIGS. 1-13 using a Luer fitting 72 for connection to a syringe or other fluid source.

FIGS. 10-12 illustrate another embodiment of lavage controller 42 having a single fluid channel 73 in fluid communication with the fluid source. The fluid source may be a syringe, comprising a standard syringe body 70 and plunger 71 that is operatively connected to lavage controller 42 via fluid fitting 72 such that it is in fluid communication with said fluid channel 73 of said lavage controller 40. Similarly to that described for the embodiment above, when the nozzle 45 of this lavage controller embodiment is docked into Y-port 60 as shown in FIGS. 10-11, the fluid-tight seal between seal 68 and nozzle 45 allows fluid communication between the syringe 70, 71 and the fitting 63 on the Y-port 60 to enable injection of medication or other fluids via the chest tube. Moreover, this fluid-tight seal prevents the fluid from escaping through the second channel 62 of the Y-port and into any suction source connected thereto; thereby preferentially going to the patient. In a preferred embodiment, the fluid fitting 72 that is operatively coupling the syringe body 70 to the lavage controller 40 is a standard Luer lock fitting. FIGS. 13 and 14 further illustrate this embodiment of a lavage controller 42 for use with one or more standard gauges of syringe that will fit the distal end of the syringe body 70 via Luer lock fitting 72 and will also fit into the first channel 61 of Y-port 60. As shown therein, nozzle 45 of this lavage controller 42 may comprise annular-exterior ribs or steps along all or part of its length to facilitate cooperative engagement with Y-port 60.

In addition to the foregoing, an integral flow meter, visual flow indicator or pressure gauge may be included to provide immediate visualization of flow. The flow indicator may be a conventional visual flow indicator such as a Bel-Art Roto-Flo™. The flow indicator may be coupled to any fluid channel. For example, flow meter can be placed in line with the fluid source via a tube to measure flow rate (rate of rotation) or even total volume (number of turns) instilled. The flow meter/indicator may optionally be linked to controller 40 to provide an electrical or mechanical auto-stop feature after it rotates a predetermined number of times. Moreover, a pressure gauge may optionally be linked to controller 40 to provide a similar auto-stop feature.

Each of the spring-return locking detent valves 46, 47 provide instantaneous control over the respective fluid flow to facilitate a pleural lavage that enables easy transition from lavage, to suction without breaking the sterile circuit. Moreover, the Y-port 60 may remain in place with a given patient for docking with lavage controller 42 at any time, for a simple and efficient to use procedure. The system employs familiar tubing connections and control valves, and establishes a rapid, automated saline infusion process, thereby minimizing training requirements and barriers to adoption. The system as a whole can be deployed at the time of thoracostomy tube placement for traumatic hemothorax to reduce the need for secondary intervention for the management of retained hemothorax.

Moreover, by using either lavage controller 40, 42 a clinician can tailor the lavage protocol (e.g., amount of infused saline per lavage cycle, and number of lavage cycles at time of tube placement) and repeat the lavage at a later time based upon clinical indications. In addition, the Y-port 60 provides flexibility for other future therapies/procedures to be administered through the chest tube without breaking the sterile circuit, such as introduction of a fibrinolytic solution, and/or the use of a balloon catheter for tube clearance and/or pneumatic agitation at the distal tip of the chest tube, etc.

Having now set forth the preferred embodiments and certain modifications of the concepts underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A system for improving fluid drainage, comprising:
a lavage controller comprised of a first lavage fluid channel and a second lavage fluid channel both in fluid communication with a nozzle, at least one valve for selectively admitting and preventing fluid flow to the nozzle from the first or second lavage fluid channels; and
a y-port comprised of:
a first fitting for connecting to an indwelling catheter;
a first y-port fluid channel operatively connected to said first fitting to enable fluid flow between said first fitting and said first y-port fluid channel; and
a second y-port fluid channel operatively connected to said first fitting to enable fluid flow between said first fitting and said second y-port fluid channel;
wherein said second y-port fluid channel is configured for connection to a first suction source and said first y-port fluid channel is configured for releasable connection to said nozzle of said lavage controller and wherein such releasable connection between said first y-port fluid channel and said nozzle disables the operative connection between said first fitting and said second y-port fluid channel.

2. A system for improving fluid drainage according to claim 1, wherein said first fitting on said y-port is comprised of at least one feature that enables connection to and grips said indwelling catheter.

3. A system for improving fluid drainage according to claim 2, wherein said at least one feature is comprised of a plurality of different diameter barbed tubing connections for connection to different diameter indwelling catheters.

4. A system for improving fluid drainage according to claim 1, further comprising at least one feature that enables tubing to be operatively connected to said second y-port fluid channel.

5. A system for improving fluid drainage according to claim 4, wherein said at least one feature is comprised of a barbed tubing connection.

6. A system for improving fluid drainage according to claim 1, further comprised of a sealing component inside said Y-port configured to facilitate said disabling of the operative connection between said first fitting and said second y-port fluid channel when said nozzle is operatively connected to said first y-port fluid channel.

7. A system for improving fluid drainage according to claim 1, further comprised of a removable cap to operatively close said first y-port fluid channel.

8. A system for improving fluid drainage according to claim 7, wherein said removable cap is further comprised of a sealing component to facilitate operative closure of said first y-port fluid channel.

9. A system for improving fluid drainage according to claim 1, wherein said lavage controller is further comprised of a second fitting that is operatively connected to said second lavage fluid channel for connection to a suction source.

10. A system for improving fluid drainage, comprising:
a lavage controller comprised of a nozzle that is operatively connected to a first lavage fluid channel; and
a y-port comprised of:
a first fitting for connecting to an indwelling catheter,
a first y-port fluid channel operatively connected to said fitting to enable fluid flow between said fitting and said first y-port channel;
a second y-port fluid channel operatively connected to said fitting to enable fluid flow between said fitting and said second y-port fluid channel;
wherein said second y-port fluid channel is configured for connection to a first suction source and said first y-port fluid channel is configured for connection to said nozzle of said lavage controller and wherein said operative connection between said first y-port fluid channel and said nozzle disables the operative connection between said fitting and said second y-port fluid channel; and
a removable cap to operatively close said first y-port fluid channel, wherein said removable cap is further comprised of a locking feature to prevent said removable cap from becoming disconnected from said first y-port fluid channel of said Y-port.

11. A system for improving fluid drainage according to claim 10, wherein locking feature on said removable cap is a projecting fastener.

12. A system for improving fluid drainage according to claim 10, wherein said locking feature comprises a protrusion on said removable cap that engages said Y-port.

13. A system for improving fluid drainage according to claim 10, wherein said removable cap is further comprised of a plug that extends inside the said first y-port fluid channel.

14. A system for improving fluid drainage according to claim 13, wherein said plug fills a first volume of said first y-port fluid channel leaving a second volume for fluid communication between said first fitting and said second y-port fluid channel, thereby preventing pooling of fluid in said first y-port fluid channel.

15. A system for improving fluid drainage according to claim 13, wherein said plug is further comprised of a sealing feature to facilitate closure of said first y-port fluid channel.

16. A system for improving fluid drainage according to claim 10, wherein said operable connection between said first fitting and said first y-port fluid channel and said second y-port fluid channel is rotatable around an axis of said fitting.

17. A system for improving fluid drainage according to claim 10, wherein lavage controller is further comprised of a second fitting that is operatively connected to said first lavage fluid channel for connection to a fluid source.

18. A system for improving fluid drainage according to claim 17, wherein said fluid source is a syringe.

19. A system for improving fluid drainage according to claim 17, wherein said fluid source is a tube connected to a fluid reservoir.

20. A system for improving fluid drainage according to claim 19, wherein said fluid reservoir is a saline bag.

21. A system for improving fluid drainage according to claim 17, further comprising a valve for managing fluid flow from said first fluid source through said first lavage fluid channel.

22. A system for improving fluid drainage according to claim 21, wherein said valve is a spring detent valve for managing pressure from said suction source through said second lavage fluid channel.

23. A system for improving fluid drainage according to claim 22, wherein said spring detent valve comprises a detent lock.

24. A system for improving fluid drainage according to claim 21, wherein said valve is a spring detent valve.

* * * * *